United States Patent
Babon et al.

[11] Patent Number: 5,851,770
[45] Date of Patent: *Dec. 22, 1998

[54] DETECTION OF MISMATCHES BY RESOLVASE CLEAVAGE USING A MAGNETIC BEAD SUPPORT

[75] Inventors: Jeff Babon; Rima Youil, both of Melbourne, Australia; Jay Stoerker, West Chester; Anne Huff, Collegeville, both of Pa.; Richard G. H. Cotton, Melbourne, Australia

[73] Assignee: Variagenics, Inc., Cambridge, Mass.

[*] Notice: The term of this patent shall not extend beyond the expiration date of Pat. No. 5,698,400.

[21] Appl. No.: 545,404

[22] Filed: Oct. 19, 1995

Related U.S. Application Data

[63] Continuation-in-part of Ser. No. 522,582, Sep. 1, 1995, abandoned, which is a continuation-in-part of Ser. No. 232,530, Apr. 25, 1994, abandoned.

[51] Int. Cl.⁶ ..................................................... C12Q 1/68
[52] U.S. Cl. ................................ 435/6; 435/18; 435/91.2; 435/91.53; 435/526; 935/78
[58] Field of Search ........................... 435/6, 91.2, 91.53, 435/810, 18; 436/526; 536/24.3, 24.33, 25.32; 935/78

[56] References Cited

U.S. PATENT DOCUMENTS

| | | | |
|---|---|---|---|
| 4,794,075 | 12/1988 | Ford et al. | 435/6 |
| 4,946,773 | 8/1990 | Maniatis et al. | 435/6 |
| 5,217,863 | 6/1993 | Cotton et al. | 435/6 |
| 5,459,039 | 10/1995 | Modrich et al. | 435/6 |
| 5,512,439 | 4/1996 | Hornes et al. | 435/6 |
| 5,698,400 | 12/1997 | Cotton et al. | 435/6 |

FOREIGN PATENT DOCUMENTS

| | | |
|---|---|---|
| WO 89/09835 | 10/1989 | WIPO . |
| WO 93/02216 | 2/1993 | WIPO . |

OTHER PUBLICATIONS

Hsu et al., Carcinogenesis 15(8):1657–1662, Aug. 1994.
Landgraf et al., Analytical Biochemistry 198:86–91, 1991.
Matthews et al. (1988) Analytical Biochemistry, vol. 169, pp. 1–25.
Allen et al., Biotechniques 7:736–44, 1989.
Bassam et al., Analytical Biochem. 196:80–83, 1991.
Bhattacharyya et al., J. Mol. Biol. 20:1191–17, 1991.
Bhattacharyya et al., Nucl. Acids Res. 17:6821–40, 1989.
Cotton, Current Biol. Ltd. 3:24–30, 1992.
Cotton, Mutation Res. 285:125–144, 1993.
Dahl et al., Am. J. Hum. Genet. 47:286–293, 1990.

(List continued on next page.)

*Primary Examiner*—Ardin H. Marschel
*Attorney, Agent, or Firm*—Clark & Elbing LLP

[57] ABSTRACT

Disclosed is a method for detecting one or more mismatches between a first and a second nucleic acid, the first and second nucleic acids being capable of preferentially hybridizing. The method involves: a) providing the first nucleic acid in its single-stranded form, the first nucleic acid being bound to the first member of a specific binding pair; b) providing the second nucleic acid in its single-stranded form, the second nucleic acid being bound to a detectably labelled reagent; c) contacting the first nucleic acid with the second nucleic acid under conditions allowing heteroduplex formation; d) contacting the product of step (c) with a magnetic bead to which is bound the second member of the specific binding pair under conditions allowing complex formation between the first and the second members of the specific binding pair; e) applying a magnetic field to the mixture to facilitate separation of the magnetic bead from the remainder of the product of step (c); f) contacting the magnetic bead-bound nucleic acid with a resolvase capable of recognizing at least one single base pair mismatch in a heteroduplex, under conditions which permit the resolvase to cleave the heteroduplex; and f) analyzing the product of step (f), the presence of a cleavage product being an indication of a mismatch between the first and second nucleic acids.

29 Claims, 6 Drawing Sheets

OTHER PUBLICATIONS

DiLella et al., The Lancet 497–99, Mar. 5, 1988.
Forrest et al., Prenatal Diagnosis 12:133–37, 1992.
Jensch et al., EMBO J. 8:4325–34, 1989.
Kemper et al., Cold Spring Harbor Symp. Quant. Biol. 49:815–25, 1984.
Kleff et al., EMBO J. 7:1527–35, 1988.
Kosak et al., Eur. J. Biochem 194:779–84, 1990.
Lilley et al., Cell 36:413–22, 1984.
Lin et al., J. Virol. Meth. 40;205–18, 1992.
Lopez–Galindez et al., PNAS USA 88:4280–84, 1981.
Lu et al., Genomics 14:249–55, 1992.
Mashal et al., Nature Genetics 9:177–83, 1995.
Mizuuchi et al., Cell 29:357–365, 1982.
Mueller et al., PNAS USA 85:9441–45, 1988.
Müller et al., Cell 60:329–36, 1990.
Parsons et al., Cell 52:621–29, 1988.
Parsons et al., J. Biol. Chem. 265:9285–89, 1990.
Pottmeyer et al., J. Mol. Biol. 223:607–15, 1992.
Shenk et al., PNAS USA 72:989–93, 1975.
Smooker et al., Biochem. 32:6443–49, 1993.
Solaro et al., J. Mol. Biol. 230:868–77, 1993.
Studier et al., Meth. Enzymol. 185:60–89, 1990.
West, Annu. Rev. Biochem. 61:603–40, 1992.
Wiebauer et al., PNAS USA 87:5842, 45, 1990.
Wu et al., PNAS USA 89:8779–83, 1992.
Yeh et al., J. Biol. Chem. 266:6480–84, 1991.
Yeh et al., J. Biol. Chem. 269:15498–504, 1994.
Youil et al., Poster Symposium, Session 40, The American Society of Human Genetics 53:1257, 1993.
Youil et al., PNAS USA 92:87–91, 1995.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCACGCGCTG GACGCGCAT        19

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AGGTGCCCTT GAGGCTGTCC        20

DETECTION OF MISMATCHES BY RESOLVASE CLEAVAGE USING A MAGNETIC BEAD SUPPORT

BACKGROUND OF THE INVENTION

This application is a continuation-in-part of Babon et al., U.S. Ser. No. 08/522,582, filed Sep. 1, 1995, now abandoned, entitled Detection of Mismatches by Resolvase Cleavage Using a Magnetic Bead Support, which is a continuation-in-part of U.S. Ser. No. 08/232,530, filed Apr. 25, 1994, now abandoned.

This invention relates to nucleic acid mismatch detection formats.

The ability to detect mutations in coding and non-coding DNA, as well as RNA, is important for the diagnosis of inherited diseases. A gene mutation can be a single nucleotide change or multiple nucleotide changes in a DNA sequence encoding an essential protein. A single nucleotide change or multiple nucleotide changes can result in frame shift mutations, stop codons, or non-conservative amino acid substitutions in a gene, each of which can independently render the encoded protein inactive. However, a gene mutation can be harmless, resulting in a protein product with no detectable change in function (i.e., a harmless gene polymorphism). Mutations in repetitive DNA can also lead to diseases as is the case, for example, in human fragile-X syndrome, spinal and bulbar muscular dystrophy, and myotonic dystrophy.

A mutant nucleic acid that includes a single nucleotide change or multiple nucleotide changes will form one or more base pair mismatches after denaturation and subsequent annealing with the corresponding wild type and complementary nucleic acid. For example, G:A, C:T, C:C, G:G, A:A, T:T, C:A, and G:T represent the eight possible single base pair mismatches which can be found in a nucleic acid heteroduplex, where U is substituted for T when the nucleic acid strand is RNA. Nucleic acid mismatches can form when the two complementary strands of a heteroduplex are derived from DNA or RNA molecules that differ in sequence such that one contains deletions, substitutions, insertions, transpositions, or inversions of sequences compared to the other.

Detection of such mutations provides an important diagnostic tool in areas including cancer diagnosis and prognosis, perinatal screening for inherited diseases, differential diagnosis of diseases not readily detectable by conventional tests (for example, Marfan's syndrome and the fragile X syndrome), and the analysis of genetic polymorphisms (for example, for genetic mapping or identification purposes).

SUMMARY OF THE INVENTION

In general, the invention features a method for detecting one or more mismatches between a first and a second nucleic acid, the first and the second nucleic acids being capable of preferentially hybridizing to each other. The method involves: a) providing the first nucleic acid in its single-stranded form, the first nucleic acid being bound to the first member of a specific binding pair; b) providing the second nucleic acid in its single-stranded form, the second nucleic acid being bound to a detectably labelled reagent; c) contacting the first nucleic acid with the second nucleic acid under conditions allowing heteroduplex formation; d) contacting the product of step (c) with a magnetic bead to which is bound the second member of the specific binding pair under conditions allowing complex formation between the first and the second members of the specific binding pair; e) applying a magnetic field to the mixture to facilitate separation of the magnetic bead and bound products from the remainder of the product of step (d); f) contacting the magnetic bead-bound nucleic acid with a resolvase capable of recognizing at least one single base pair mismatch in a heteroduplex, under conditions which permit the resolvase to cleave the heteroduplex; and g) analyzing the product of step (f), the presence of a cleavage product being an indication of a mismatch between the first and the second nucleic acids.

In a related aspect, the invention features a second method for detecting one or more mismatches between a first and a second nucleic acid, the first and the second nucleic acids being capable of preferentially hybridizing to each other, involving: a) providing the first nucleic acid in its single-stranded form, the first nucleic acid being bound to the first member of a specific binding pair; b) providing the second nucleic acid in its single-stranded form; c) contacting the first nucleic acid with the second nucleic acid under conditions allowing heteroduplex formation; d) contacting the product of step (c) with a magnetic bead to which is bound the second member of the specific binding pair under conditions allowing complex formation between the first and the second members of the specific binding pair; e) applying a magnetic field to the mixture to facilitate separation of the magnetic bead and bound products from the remainder of the product of step (d); f) contacting the magnetic bead-bound nucleic acid with a resolvase capable of recognizing at least one single base pair mismatch in a heteroduplex, under conditions which permit the resolvase to cleave the heteroduplex; and g) analyzing the supernatant of step (f) (for example, by electrophoresis followed, for example, by silver staining), the presence of a cleavage product being an indication of a mismatch between the first and the second nucleic acids.

In another related aspect, the invention features a third method for detecting one or more mismatches between a first and a second nucleic acid, the first and second nucleic acids being capable of preferentially hybridizing to each other, involving: a) providing the first nucleic acid in its single-stranded form, the first nucleic acid being bound to the first member of a specific binding pair; b) providing the second nucleic acid in its single-stranded form; c) contacting the first nucleic acid with the second nucleic acid under conditions allowing heteroduplex formation; d) contacting the product of step (c) with a magnetic bead to which is bound the second member of the specific binding pair under conditions allowing complex formation between the first and the second members of the specific binding pair; e) applying a magnetic field to the mixture to facilitate separation of the magnetic bead and bound products from the remainder of the product of step (d); f) contacting the magnetic bead-bound nucleic acid with a resolvase capable of recognizing at least one single base pair mismatch in a heteroduplex, under conditions which permit the resolvase to cleave the heteroduplex; g) labeling the product of step (f) not bound to the magnetic bead with a detectable label; and h) analyzing the labeled product, the presence of a cleavage product being an indication of a mismatch between the first and the second nucleic acids.

In yet another related aspect, the invention features a method for detecting one or more mismatches between a first and a second nucleic acid, the first and the second nucleic acids being capable of preferentially hybridizing to each other. The method involves: a) providing the first nucleic acid in its single-stranded form, the first nucleic acid being bound to the first member of a specific binding pair; b) providing the second nucleic acid in its single-stranded form, the second nucleic acid being bound to a detectably labelled reagent; c) contacting the first nucleic acid with the second nucleic acid under conditions allowing heteroduplex formation; d) contacting the product of step (c) with a magnetic bead to which is bound the second member of the specific binding pair under conditions allowing complex formation between the first and the second members of the specific binding pair; e) applying a magnetic field to the mixture to facilitate separation of the magnetic bead and bound products from the remainder of the product of step (d); f) contacting the magnetic bead-bound nucleic acid with a resolvase capable of recognizing at least one single base pair mismatch in a heteroduplex, under conditions which permit the resolvase to cleave the heteroduplex; and g) analyzing the product found in the sample supernatant of step (f), the presence of a cleavage product being an indication of a mismatch between the first and the second nucleic acids.

In preferred embodiments of one or more of the above aspects, the magnetic bead is a Dynabead; the nucleic acid is dissociated from the magnetic bead prior to cleavage product analysis; the product of step (f) is analyzed by gel electrophoresis, on an automated sequencing apparatus, by radioactive scintillation counting or fluorescence detection, or by any other detectable signal intensity method; the resolvase is bacteriophage T4 endonuclease VII; the first and/or the second nucleic acid is the product of PCR amplification; the first nucleic acid is PCR amplified using at least one primer labelled (for example, 5' end labelled) with the first member of the specific binding pair; the first nucleic acid is amplified using one primer labelled (for example, 5' end labelled) with the first member of the specific binding pair and a second primer which is unlabelled; the specific binding pair is avidin (for example, streptavidin) and biotin; the first and/or the second nucleic acids are rendered single-stranded by denaturation; the second nucleic acid is the product of PCR amplification using a primer which is detectably labelled (for example, with a radioactive or fluorescent label); the second nucleic acid is amplified using a pair of PCR primers, the first PCR primer being labelled with a first detectable label and the second PCR primer being labelled with a second detectable label; the mismatch results from a mutation or polymorphism; and one of the first or the second nucleic acids is a reference nucleic acid and the other is a test nucleic acid.

In another related aspect, the invention features a kit for detecting a mismatch in a test nucleic acid, the kit including: a) a magnetic bead to which is bound one member of a specific binding pair; and b) a resolvase which is capable of recognizing and cleaving at least one single base pair mismatch in a complementary heteroduplex pair.

In preferred embodiments, the kit further includes a reference nucleic acid which preferentially hybridizes to the test nucleic acid, the reference nucleic acid being capable of binding to the second member of the specific binding pair; the kit further includes a pair of PCR primers, at least one primer of the pair being capable of binding to the second member of the specific binding pair; the kit further includes a pair of PCR primers, at least one primer of the pair being bound to a detectable label; the specific binding pair is avidin (for example, streptavidin) and biotin; the resolvase is bacteriophage T4 endonuclease VII; the magnetic bead is a Dynabead; and the mismatch results from a mutation or polymorphism.

By the term "heteroduplex" is meant a structure formed between two annealed, complementary nucleic acid strands (e.g., the annealed strands of test and reference nucleic acids) in which one or more nucleotides in the first strand are unable to appropriately base pair with those in the second opposing, complementary strand because of one or more mismatches. Examples of different types of heteroduplexes include those which exhibit an exchange of one or several nucleotides, and insertion or deletion mutations, each of which is disclosed in Bhattacharya and Lilley, Nucl. Acids. Res. 17: 6821 (1989). The term "complementary," as used herein, means that two nucleic acids, e.g., DNA or RNA, contain a series of consecutive nucleotides which are capable of forming matched Watson-Crick base pairs to produce a region of double-strandedness. Thus, adenine in one strand of DNA or RNA pairs with thymine in an opposing complementary DNA strand or with uracil in an opposing complementary RNA strand. Or guanine in one strand of DNA or RNA pairs with cytosine in an opposing complementary strand. The region of pairing is referred to as a duplex. A duplex may be either a homoduplex or a heteroduplex.

The term "mismatch" means that a nucleotide in one strand of DNA or RNA does not or cannot pair through Watson-Crick base pairing and π-stacking interactions with a nucleotide in an opposing complementary DNA or RNA strand. Thus, adenine in one strand of DNA or RNA would form a mismatch with adenine in an opposing complementary DNA or RNA strand. Mismatches also occur where a first nucleotide cannot pair with a second nucleotide in an opposing complementary DNA or RNA strand because the second nucleotide is absent (i.e., one or more nucleotides are inserted or deleted). This latter structure is sometimes referred to as a loop and is also a substrate for the resolvases described herein.

As used herein, the phrase "preferentially hybridizes" refers to a nucleic acid strand which anneals to and forms a stable duplex, either a homoduplex or a heteroduplex, under normal hybridization conditions with a second complementary nucleic acid strand, and which does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction (see, for example, Ausubel et al., *Current Protocols in Molecular Biology,* John Wiley & Sons, Inc., New York, or Sambrook et al., *Molecular Cloning: A Laboratory Manual,* Cold Spring Harbor Laboratory Press).

As used herein, a "magnetic bead" is any solid support that is attracted by a magnetic field; such solid supports include, without limitation, Dynabeads, BioMag Streptavidin, MPG® Streptavidin, Streptavidin Magnesphere™, Streptavidin Magnetic Particles, AffiniTip™, any of the Maga line of magnetizable particles, BioMag Superparamagnetic Particles, or any other magnetic bead to which a specific binding pair member may be attached or immobilized.

As used herein, a "resolvase" is any protein capable of recognizing and cleaving a mismatch (for example, a mismatch loop) in a heteroduplex template. Examples of resolvases include, without limitation, T4 endonuclease VII, *Saccharomyces cerevisiae* Endo X1, Endo X2, or Endo X3 (Jensch et al., EMBO J. 8:4325, 1989), T7 endonuclease I, *E. coli* MutY (Wu et al., Proc. Natl. Acad. Sci. USA 89:8779–8783, 1992), mammalian thymine glycosylase (Wiebauer et al., Proc. Natl. Acad. Sci. USA 87:5842–5845, 1990), topoisomerase I from human thymus (Yeh et al., J. Biol. Chem. 266:6480–6484, 1991; Yeh et al., J. Biol. Chem. 269:15498–15504, 1994), and deoxyinosine 3' endonuclease (Yao and Kow, J. Biol. Chem. 269:31390–31396, 1994). In a given mismatch detection assay, one or several resolvases may be utilized.

By "specific binding pair" is meant any pair of molecules, including a first and a second member, which have a specific, covalent or noncovalent affinity for each other. Examples of specific binding pairs include antigen/antibody pairs, DNA binding protein/DNA binding site pairs, enzyme/substrate pairs, lectin/carbohydrate pairs, and nucleic acid duplexes or ligated DNA strands. A preferred specific binding pair of the invention is avidin (for example, streptavidin) and biotin.

A "mutation," as used herein, refers to a nucleotide sequence change (i.e., a single or multiple nucleotide substitution, deletion, or insertion) in a nucleic acid sequence. A nucleic acid which bears a mutation has a nucleic acid sequence that is different in sequence from that of the corresponding wild-type population. The methods of the invention are especially useful in detecting a mutation in a test nucleic acid which contains between 1 and 50 nucleotide sequence changes (inclusive). Preferably, a mutation in a test or reference nucleic acid will contain between 1 and 10 nucleotide sequence changes (inclusive), and more preferably between 1 and 7 nucleotide sequence changes (inclusive).

A "reference nucleic acid," as used herein, is any sequence of DNA or RNA that is at least 20 nucleotides in length, preferably between 100 and 40,000 nucleotides in length, and more preferably between 150 and 5000 nucleotides in length. Often, the reference nucleic acid will have a sequence that is indistinguishable from DNA obtained from a corresponding wild-type population.

A "test nucleic acid" is any sequence of DNA or RNA that is at least 20 nucleotides in length, preferably between 100 and 40,000 nucleotides in length, and more preferably between 150 and 5000 nucleotides in length. When particularly large test nucleic acid fragments are analyzed (i.e., larger than 2 kb), the nucleic acid may be cleaved with a second restriction enzyme in order to obtain a fragment of a size suitable for denaturing polyacrylamide gel electrophoresis (<2 kb). The choice of a second restriction enzyme will be guided by creating a restriction enzyme map of the DNA fragment.

If desired, the test or reference nucleic acids may be isolated prior to carrying out the detection assay. By an "isolated nucleic acid" is meant a nucleic acid segment or fragment which is not immediately contiguous with (i.e., covalently linked to) both of the nucleic acids with which it is immediately contiguous in the naturally occurring genome of the organism from which the nucleic acid is derived. The term, therefore, includes, for example, a nucleic acid which is incorporated into a vector, for example, a bacteriophage, virus, or plasmid vector capable of autonomous replication. The term "isolated nucleic acid" may also include a nucleic acid which is substantially purified from other nucleic acids, such as a nucleic acid fragment produced by chemical means, selective amplification, or restriction endonuclease treatment. Because the detection assays of the invention may be used to simultaneously analyze more than one DNA sequence, isolation and purification are not required, but may be carried out if desired.

As disclosed herein, this invention provides a simple and inexpensive means for detecting DNA mismatches in nucleic acid samples. This approach is extremely useful for detecting DNA mutations associated with mammalian diseases (such as cancer and various inherited diseases). In particular examples, one or more mutations in repetitive DNA is associated with the human fragile-X syndrome, spinal and bulbar muscular dystrophy, and myotonic dystrophy (Caskey, supra). Repetitive DNA from each of these genes can serve as test nucleic acids in the methods described herein. Alternatively, the methods of the invention may be used to detect mutations corresponding to diseases (for example, Marfan's syndrome) for which a standard test is not available or is inconclusive. The methods are also useful for forensic applications or the identification of useful traits in commercial (for example, agricultural) species. The simple, rapid, and sensitive nature of the claimed methods and their ability to be readily automated renders them practical for large scale screening of many samples or for screening a particular sample against a number of reference nucleic acids.

Those skilled in the art will recognize that the invention is also useful for other purposes. For example, the claimed method facilitates detection of single base pair mismatches in cloned DNA, for example, mutations introduced during experimental manipulations (e.g., transformation, mutagenesis, PCR amplification, or after prolonged storage or freeze:thaw cycles). This method is therefore useful for testing genetic constructs that express therapeutic proteins or that are introduced into a patient for gene therapy purposes.

The method may also be used for rapid typing of bacterial and viral strains. By "type" is meant to characterize an isogeneic bacterial or viral strain by detecting one or more nucleic acid mutations that distinguishes the particular strain from other strains of the same or related bacteria or virus. As an example, genetic variation of the human immunodeficiency virus has led to the isolation of distinct HIV types, each bearing distinguishing gene mutations (Lopez-Galindez et al., Proc. Natl. Acad. Sci. USA 88:4280 (1991)). Other examples of test DNAs of particular interest for typing include test DNAs isolated from viruses of the family Retroviridae, for example, the human T-lymphocyte viruses or human immunodeficiency viruses (in particular any one of HTLV-I, HTLV-II, HIV-1, or HIV-2), DNA viruses of the family Adenoviridae, Papovaviridae, or Herpetoviridae, bacteria, or other organisms, for example, organisms of the order Spirochaetales, of the genus Treponema or Borrelia, of the order Kinetoplastida, of the species *Trypanosoma cruzi*, of the order Actinomycetales, of the family Mycobacteriaceae, of the species *Mycobacterium tuberculosis*, or of the genus Streptococcus.

Unless otherwise defined, all technical terms and scientific terms used herein have the same meaning as commonly understood by one of ordinary skill in the art to which this invention belongs. All publications mentioned herein are incorporated by reference.

Other features and advantages of the invention will be apparent from the following description of the detailed description and from the claims.

DETAILED DESCRIPTION

The drawings will first briefly be described.

Drawings

Figure 7A:
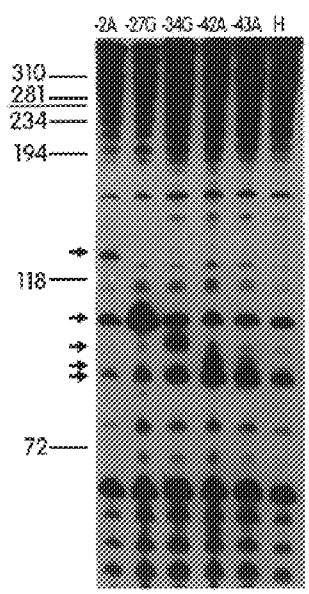
Figure 7B:
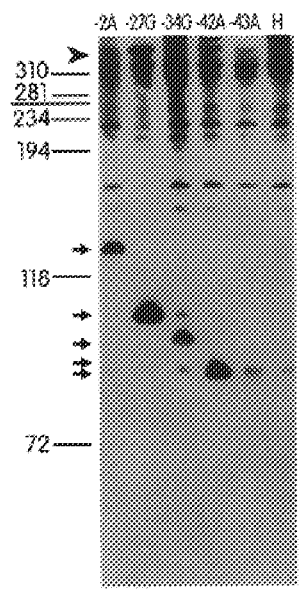
Figure 7C:
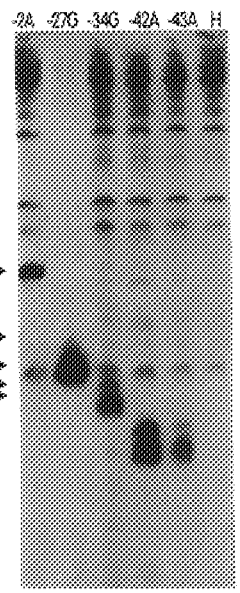

FIGS. 7A–C are gel photographs showing a comparison of the signal to noise ratio of conventional and modified enzyme mismatch cleavage techniques. In particular, enzyme mismatch cleavage was performed on five different heteroduplexes (-2A, -27G, -34G, -42A, -43A) and a homoduplex control (H). FIG. 7A shows conventional enzyme mismatch cleavage conditions. FIG. 7B shows modified enzyme mismatch cleavage conditions (as described herein). And FIG. 7C shows modified enzyme mismatch cleavage conditions performed on the same five mutations, but using only one biotinylated PCR primer to amplify the mutant clones (as described herein). The expected cleavage fragment sizes are as follows: -2A, 421 & 125 bp; -27G, 446 & 100 bp; -34G, 453 & 93 bp; -42A, 461 & 85 bp; -43A, 462 & 84 bp. Each mutation results in a small (→) and a large (▸, not well resolved) cleavage fragment. The method used in FIG. 7C, however, detects only one of the two cleavage products. The large cleavage products are not easily visible in FIG. 7A due to the high background cleavage level and thus are not marked.

There now follows exemplary nucleic acid mismatch detection methods utilizing T4 endonuclease VII and a magnetic bead-based protocol. These examples are provided for the purpose of illustrating, not limiting, the invention.

T4 Endonuclease VII Cleavage of Products Bound to Dynabeads

In a preferred method according to the invention, the first and second nucleic acids (i.e., test and reference nucleic acids or mutant and wild-type nucleic acids) are PCR amplified by standard techniques, with one of the PCR products being bound to a first member of a specific binding pair (for example, bound to biotin at the 5' end) and the other PCR product being detectably labelled (either before or after cleavage, for example, with fluorescein, a radioactive label, or any other detectable label, or with two different fluorophores). Following mixing and denaturation of the test and reference PCR products, heteroduplex formation is allowed to occur, and biotinylated products are captured by binding to streptavidin-magnetic beads (with streptavidin being the second member of the specific binding pair). Application of a magnetic field concentrates and isolates these beads, and captured heteroduplexes are then cleaved by resolvase treatment, and the labelled products analyzed, for example, by standard gel electrophoretic methods, scintillation counting, fluorescence detection, on an automated laser fluorescence DNA sequencer, or by any other detectable signal intensity method (FIGS. 1–6). If a mismatch exists between the two nucleic acids, this is indicated by cleavage fragment size and can be confirmed and defined by DNA sequencing. The extent of cleavage can be determined by comparing the intensity of the full-length band to the intensity of the cleavage band(s).

In the above technique, four species of duplex are formed: two different heteroduplexes and the two original homoduplexes. The exact nature of the species captured by the magnetic beads depends on the extent of biotinylation. In one embodiment (shown, for example, in FIGS. 1 and 2), a single biotinylated PCR primer is utilized in the amplification steps, and a single nucleic acid strand is therefore available for magnetic bead capture. In this embodiment, only one of the two heteroduplex species is ultimately bound to the magnetic bead support, and only those cleavage fragments are detected. In an alternative embodiment (shown, for example, in FIGS. 5 and 6), both members of the PCR primer pair are biotinylated, thereby enabling capture of both heteroduplex species and detection of all labelled cleavage fragments.

In either embodiment, one homoduplex species is unlabelled and is therefore undetectable (even though it may be captured), and the other homoduplex is not bound to biotin and is therefore not captured at all. Accordingly, by using this technique, labelled homoduplex DNA is discarded, while heteroduplex DNA is captured and detected. This dramatically decreases background signal that results largely from non-specific cleavage of labelled homoduplex DNA or low yield heteroduplex DNA (for example, in a heterozygous mutant), thereby increasing the sensitivity and specificity of the mismatch cleavage assay.

In more detail, this approach is carried out as follows.

DNA Amplification, Purification, and Quantitation

PCR products are generated by standard techniques (see, for example, Ausubel et al., *Current Protocols in Molecular Biology*, John Wiley & Sons, Inc., New York, or Sambrook et al., *Molecular Cloning: A Laboratory Manual*, Cold Spring Harbor Laboratory Press) with the primers labelled as follows. For the first nucleic acid sample (for example, the reference or wild-type DNA), one of the following pairs of PCR primers is used: for radioactivity-based assays, one 5'-biotinylated primer and one unmodified primer, or two biotinylated primers; or, for fluorescence-based assays, one 5'-biotinylated primer and one unmodified primer, or two biotinylated primers. For the second nucleic acid sample (for example, the test or mutant DNA), a corresponding set of primers is chosen and labelled as follows: for radioactivity-based assays, primers with 5' OH's are utilized to permit subsequent 5'-radiolabeling, or, for fluorescence-based assays, a 5'-fluoresceinated primer is utilized for amplification of the strand complementary to the wild-type biotinylated strand in combination with one unmodified primer. DNA amplification conditions are optimized by standard techniques for each primer set with respect to concentrations of $Mg^{+2}$, DNA template, and primers; conditions for use with unmodified primers sometimes differ from those for use with biotinylated or fluoresceinated primers.

Following amplification, a small sample (sample #1) from each amplification reaction may be withdrawn and set aside. From the remaining mixture, reaction salts and unincorporated primers are removed by applying the mixture to a molecular-weight-cut-off spin column, such as the QIAGEN QiaQuick PCR Purification kit (Chatsworth, Calif.) or the Amicon Microcon-30 (Amicon, Beverly, Mass.) column and following manufacturer's instructions for column use and capacity. If desired, a second small sample (sample #2) may be withdrawn from the recovered DNA solution, and the efficiency of primer removal and of DNA recovery determined by electrophoresing samples #1 and #2 through a 19:1 acrylamide or agarose gel and visualizing DNA by ethidium bromide staining.

DNA concentrations may then be determined by any standard method. For example, the amplified DNA may be electrophoresced along with the GIBCO BRL Mass Ladder (according to the manufacturer's instructions; GIBCO, Grand Island, N.Y.), preferably using three different amounts of the amplification reactions and three different amounts of the Mass Ladder to provide a series of DNA quantities. The resultant gel is then ethidium bromide stained, the destained gel photographed, and the amplified DNA relative to the Mass Ladder standards quantitated by densitometry of the resulting negative.

Substrate Preparation for Radioactivity-Based Assays

To prepare a PCR product for use in a radioactivity-based assay, the unmodified (for example, wild-type or reference) DNA is radiolabeled. Such labeling may be accomplished by end-labeling (for example, 5'-end labeling using bacteriophage T4 polynucleotide kinase and [$\gamma$-$^{32}$P]ATP) or by uniform labeling using any radioactive dNTPs of choice. Standard protocols for these techniques are provided, for example, in *Molecular Cloning*, supra, or *Current Protocols in Molecular Biology*, supra. The specific activity of each radiolabeled DNA is then determined (for example, as described in *Molecular Cloning*, supra, or *Current Protocols in Molecular Biology*, supra. In the Endo VII protocol, specific activity is defined as total TCA precipitable counts per quantity of precipitated DNA. A specific activity equal to or greater than 1600 dps/pmole is recommended.

To remove unincorporated [$\gamma$-$^{32}$P]ATP or radioactive dNTPs, the radiolabeled sample is passed through a gel filtration resin such as Sephadex G-50 (Pharmacia, Piscataway, N.J.), as described in either *Molecular Cloning*, supra, or *Current Protocols in Molecular Biology*, supra. Recovery from the spin-column is determined by performing scintillation counting on a small sample of the flow-thru volume and calculating the percent of applied DNA recovered, based on the previously determined specific activity of the DNA.

Determination of Automated Sequencer Detection Limits for Fluoresceinated Amplification Products The percentage of a given preparation of fluorescein-labeled primer that actually contains fluorescein (or the "specific activity" of this primer) is variable. This variation is manifested as differing specific activities for fluorescein-tagged amplification products. Accordingly, prior to use of a fluorescein-tagged amplification product as an Endo VII substrate, a determination of the detection limits of an automated sequencer for each amplification product is recommended. This determination may be accomplished by quantitating the sequencer response for a series of fluorescein-tagged amplification products (both wild-type and mutant nucleic acids).

Formation of Biotinylated Heteroduplexes

To allow formation of heteroduplexes between two nucleic acids (for example, test and reference nucleic acids or wild-type and mutant nucleic acids), purified PCR products from the test and reference reactions are combined in any standard DNA annealing buffer (for example, 10 mM Tris containing up to 0.5M NaCl or 2–50 mM MgCl$_2$; 15 mM sodium citrate buffer; or, preferably, 10 mM Tris-HCl, pH 8.0, 1 mM EDTA, pH 8.0, brought to a final pH of 7.5 with 2N HCl and containing 2–50 mM (and, preferably, 10 mM) MgCl$_2$). These PCR products are mixed at an appropriate ratio (for example, in equimolar amounts), and the reaction is carried out in a thin walled, heat resistant tube (for example, a 500 $\mu$L heat resistant tube). At least 2 pM of each product in an approximately 10 $\mu$L volume is recommended, but larger volumes and a range of 1–10 pM of product are also useful if appropriate DNA concentrations are maintained. Total volumes larger than 40 $\mu$L are not recommended.

The surface of the reaction mixture is covered with a small volume of sterile mineral oil, and the samples heated to greater than 95° C. in either a heat block or in 500 mL of boiling water for 5 minutes. Following incubation, the samples are allowed to cool to 50° C. (for example, by placing the heat block or beaker of water at room temperature (for example, on a benchtop) and allowing cooling, for example, over a 30–40 minute interval). Once samples reach 50° C., they are placed into ice until use. Heteroduplexes can be stored refrigerated at 4° C. for several days, but preferably are stored frozen.

As an alternative method for heteroduplex formation, a thermal cycler may be programmed to heat 5 minutes at 95° C. and then to slow cool to 65° C. at 1° C. per minute. At the end of the program, the samples are placed on ice until use.

Solid Phase Binding

As a first step toward binding the heteroduplexed DNA to the streptavidin-magnetic beads, these beads (preferably, Dynabeads M-280 Streptavidin; Dynal, Oslo, Norway) are washed as recommended by the manufacturer to remove preservatives which may interfere with performance. The Dynabeads M-280 Streptavidin are then resuspended by gently shaking to obtain a homogeneous suspension, and a quantity appropriate for the desired number of assays (preferably, between 0.75–20 $\mu$l per assay and, more preferably, 10 $\mu$L per assay) removed to a tube. The tube is then placed in a strong magnetic support (for example, a Dynal® MPC-9600) for at least 30 seconds, and the supernatant removed by aspiration, being careful not to disturb the Dynabeads. An equal volume of PBS, pH 7.4 (i.e., 8 g NaCl, 0.2 g KCl, 1.44 g Na$_2$HPO$_4$, 0.24 g KH$_2$PO$_4$ in 1000 ml of ddi H$_2$O, brought to a final pH of 7.4 with 2N HCl) containing 0.1% BSA is then added, the beads gently shaken, recontacted with the magnetic support, and allowed to clear from suspension for at least 30 seconds. The supernatant is then removed by aspiration, again being careful not to disturb the Dynabeads. A volume of Binding Buffer (10 mM Tris, 1 mM EDTA, 1M NaCl, pH 7.6) equal to twice the original bead volume is then added, the Dynabeads gently resuspended, and 20 $\mu$L added to each reaction tube. The reaction tubes (containing the Dynabeads) are then placed in the magnetic holder and allowed to stand at least 30 seconds while the binding reaction is prepared.

To prepare the binding reaction, 5 $\mu$L of the heteroduplex/homoduplex DNA solution (containing between 1.0 pM and 10 pM, and preferably approximately 2.0 pM, of the biotinylated heteroduplex) is added to 15 $\mu$L of TE, optionally containing up to 1.0M NaCl. A larger volume can be used if the ratio of DNA solution to TE/NaCl is maintained.

After concentrating the Dynabeads with a magnet, the supernatant is removed by pipetting, and 20 $\mu$L of DNA solution is added to each reaction tube. The mixture is incubated at room temperature (22°–26° C.) for 30 minutes, with gentle manual agitation every 10 minutes, or, alternatively, for multiple samples, using a Dynal® PC®-9600 microplate. If the microplate is used, the tubes (up to 48) are allowed to stand outside the microplate for 10 minutes, are placed in the manufacturer's indicated "A" position for 1 minute, and are then switched to the manufacturer's indicated "B" position for 1 minute. The tubes are then returned to a position outside the microplate, and the process is repeated after 10 minutes, with the tubes being allowed to stand 10 minutes between steps.

Prior to contact with the Endo VII enzyme, the DNA-bound Dynabeads are concentrated using the magnetic stand, and the bead-free supernatant removed. The beads are then washed twice with 50 µl of Endo VII reaction buffer (1× concentration; see below). After the first wash, the beads are magnet-concentrated, and the supernatant removed. After the second wash, the beads are again concentrated, but the supernatant is left in contact with the beads until immediately prior to use in the Endo VII reaction.

T4 Endonuclease VII Production

T4 Endonuclease VII may be obtained commercially from Applied Technology Genetics Corp. (Malvern, Pa.).

Alternatively, the enzyme may be prepared by the method of Kosak and Kemper, Eur. J. Biochem. 194:779–784 (1990), or preferably is prepared by inducible expression and purification as follows (see also Kemper, Preparation of Recombinant Resolvases, U.S. Ser. No. 60/003,104, filed Sep. 1, 1995, hereby incorporated by reference).

The T4 gene 49 encoding endonuclease VII is amplified from genomic T4 GT7dc DNA by polymerase chain reaction, and the resulting PCR product digested with StuII and BglII and ligated into vector pET-11a (Studier et al., Meth. Enzymol. 185: 60–89, 1991) according to standard techniques. The resulting plasmid (pRB210) is then transformed into $E.$ $coli$ strain BL21(DE3).

Endonuclease VII encoded by the pRB210 plasmid is then inducibly expressed as follows. A 500 ml culture of BL21 (DE3) transformed with pRB210 is used to inoculate a fermenter containing 8 l of LB/ampicillin medium. Cells are grown at 30° C. under continuous stirring (600 rpm) and heavy aeration (5 l/min). At a cell density of approximately $5 \times 10^7$ cells/ml ($OD_{550}$=0.8), expression of the T4 gene 49 encoding endonuclease VII is induced by the addition of isopropyl-1-thio-β-D-galactoside (IPTG) to a final concentration of 1 mM. After 2 hours, cells are harvested by centrifugation and immediately frozen at −80° C.

Endonuclease VII is purified from the IPTG-induced BL(DE3) cells as follows. Approximately 25 g of frozen BL21(DE3) cells are thawed in 100 ml of Buffer A (10 mM Tris/HCl, pH 8.0, 10 mM $MgCl_2$, 1 mM EDTA, 2 mM phenylmethylsufonylfluoride (PMSF), 10% glycerol (by volume) and 10 mM 2-mercaptoethanol (ME)) and then sonicated for 30 minutes at a setting of 5 with a Branson sonifer equipped with a 0.5 cm tip. To obtain a clear crude extract, insoluble cell debris is removed by centrifugation at 100,000×g for 45 minutes. To 100 ml of cleared crude extract, 30.2 ml polyethyleneglycol (PEG) 6000 (from a 30% (mass./vol.) stock-solution) and 11.2 ml of dextran T500 (from a 20% (mass./vol.) stock-solution both in Buffer A) is added. Finely ground NaCl is then slowly added, with stirring, to a final concentration of 4M. The resulting suspension is stirred for an additional 1 hour. Next, the PEG and dextran phases are separated by low speed centrifugation (30 min., 10,000×g) using a Sorvall SS34 rotor. The top phase, containing PEG and protein, is removed and dialyzed overnight against 8 l of Buffer B (10 µM Tris/HCl, pH 8.0, 2 mM EDTA, 10 mM ME, and 10% glycerol (by vol.)) containing 300 mM KCl. After dialysis, the solution is cleared by low speed centrifugation. The resulting supernatant is referred to as Fraction II.

Fraction II is then loaded onto a 40 ml heparin-agarose column equilibrated with Buffer B containing 300 mM KCl. After loading, the column is washed with 4 bed volumes of the same buffer, and the protein is eluted with five bed volumes of a linear gradient of 300–700 mM KCl in Buffer B at a flow rate of 1.5 ml/min. Fractions (5 ml) are collected and evaluated for endonuclease VII activity according to standard methods. Endonuclease VII activity is generally found in fractions having greater than 520 mM KCl. Fractions containing endonuclease VII activity are then pooled and dialyzed overnight against 8 l Buffer B containing 50 mM KCl. The dialyzed pooled fractions of endonuclease VII activity are referred to as Fraction III.

Next, Fraction III is loaded onto a Mono-Q column (HR 10/10) equilibrated with Buffer B containing 50 mM KCl. After loading, the column is washed with 4 bed volumes of Buffer B containing 50 mM KCl, and the protein is eluted with 8 bed volumes of a linear gradient of 50–1000 mM KCl in Buffer B at a flow rate of 0.8 ml/min. Fractions (1 ml) are collected and evaluated for endonuclease VII activity according to standard methods. The majority of the endonuclease VII activity generally appears in the range of 150 mM to 250 mM KCl. Fractions having endonuclease VII activity are pooled and stored in 50% glycerol at −20° C.

Mismatch Cleavage by Bacteriophage T4 Endonuclease VII

To digest bound DNA with T4 endonuclease VII (endo VII), the enzyme is first diluted to the desired concentration. Endo VII is supplied at an activity concentration of 500 units/µl (Applied Technology Genetics Corp., Malvern, Pa.). 125 units of Endo VII (in a volume of 3 µl) is recommended for a reaction containing 170 fmoles of bound heteroduplex substrate DNA. For high activity dilutions, Endo VII 50% glycerol-based storage buffer (i.e., 10 mM Tris, pH 8.0, 5 mM DTT (or 0.1 mM glutathione and 100 µg/ml BSA), 50% glycerol) is used; this buffer allows for high activity dilutions that may subsequently be stored at −20° C. (to conserve enzyme activity). For low activity dilutions, Endo VII 20% glycerol-based dilution buffer (i.e., 10 mM Tris, pH 8.0, 5 mM DTT, 20% glycerol) is used; enzyme diluted into this dilution buffer is not stable upon storage and should be used immediately.

Endo VII reactions on bound DNA are carried out as follows. 13 µl of water, 4 µl 5× Endo VII reaction buffer (i.e., 50 mM Tris, pH 8.0, 10 MM $MgCl_2$, 5 mM DTT, 100 µg/ml BSA), and 3 µl Endo VII (125 units/3 µl) are combined, in this order. The supernatant is removed from the second Dynabead wash, and 20 µl of the Endo VII reaction mix is added to each tube of Dynabead-bound DNA. The beads are mixed, either manually or by following the manufacturer's instructions for the Dynal® MPC-9600 microtitre tray. The reactions are incubated at 37° C. for one hour, agitating the beads every 10 minutes. As a general guide, treatment of 170 fmoles of bead-bound 500-mer with 125 units of Endo VII results in 95% substrate cleavage. In these reactions, it may be necessary to modify the suggested enzyme/DNA quantities based on the particular DNA substrate, the substrate length, and/or the volume of beads.

Control reactions are carried out exactly as above except the reaction mixture lacks Endo VII enzyme (i.e., enzyme is replaced by enzyme dilution buffer). Additional control reactions that include known homoduplex DNA (for example, wild-type DNA reacted with wild-type DNA) and known heteroduplex DNA, with and without Endo VII enzyme, may also be carried out. Each reaction is agitated every 10 minutes (as described above). The control reactions demonstrate the amount of intact bead-bound substrate DNA available for Endo VII cleavage and also provide a test for nuclease activity present in the reaction mix.

Alternative Endo VII cleavage reaction conditions are described in Youil et al., Proc. Natl. Acad. Sci. USA 92:87–91 (1995) or Mashal et al., Nature Genetics 9:177 (1995).

Quantitation of Cleavage Product in Sample Supernatant

The extent of Endo VII cleavage may be determined directly by quantitating an aliquot of the reaction sample supernatant obtained above. According to this approach, all or a portion of the supernatant (for example, 5–10 µl) is isolated, and the amount of cleaved product in that supernatant determined by standard methods of scintillation counting (for radioactive samples) or fluorescence detection, for example, using a fluorometer or microtiter plate fluorescence reader (for fluorescent samples).

Using this technique and a radiolabeled mismatch-containing substrate, the data shown in Table 1 was obtained.

TABLE 1

| Units T4eVII | cpm on Beads cpm1 | pM Bound cpm1/S.A. | Cleavage cpm (cpm2) | % Cleaved |
|---|---|---|---|---|
| 0 | 6612 | 0.179 | 736 | 11 |
| 50 | 6244 | 0.169 | 4808 | 77 |
| 125 | 6622 | 0.184 | 6480 | 95 |
| 250 | 6384 | 0.173 | 6136 | 96 |
| Mean | 6516 | 0.176 | | |
| S.D. | 255 | 0.007 | | |
| % CV | 3.9 | 4 | | |

Specific Activity = 37000 cpm/pm

As shown in Table 1, detection of labeled cleavage product in sample supernatants increased with increasing Endo VII concentration and was highly efficient at 125 units or more of enzyme.

Silver Staining of Cleavage Product

In an alternative detection technique, the cleavage products are separated by polyacrylamide gel electrophoresis and visualized by silver staining as described, for example, in Allen et al, BioTechniques 7:736 (1989) or Bassam et al., Anal. Biochem. 196:80 (1991). By this technique, the use of detectable labels (such as radioactivity) may be avoided.

Electrophoresis and Detection of Labeled Cleavage Product

Another detection approach involves electrophoresis of labeled products. In this technique, labeled cleavage products are recovered from the above reaction mix as follows. For radioactivity-based assays, an equal volume (20 µl) of 95% formamide containing 20 mM EDTA, pH 8.0, 0.05% xylene cyanol, and 0.05% bromophenol blue is added to the mix, and the sample is heated at 95° C. for 3 minutes to inactivate Endo VII. The sample is then placed on ice. For fluorescence-based assays, an equal volume (20 µl) of 100% formamide containing 375 mg/ml crystal violet is added to the mix, and again the sample is heated at 95° C. for 3 minutes and then placed on ice.

For samples labeled with a fluorescent marker, analysis using an automated sequencing system is recommended (for example, an ALF sequencer, available from Pharmacia Biotech AB, Uppsala, Sweden). As indicated above, fluorescently labeled oligonucleotide primer species vary somewhat in specific activity and therefore in signal intensity. Accordingly, if desired, a preliminary electrophoretic run and titration of any new primer may be carried out. An optimal signal intensity should be achieved with under 1 pM of primer.

A variety of gel matrices may be used for the electrophoresis of fluorescent product, provided that the materials show no auto-fluorescence. A 19:1 acrylamide:bis-acrylamide gel mixture and Long Ranger gel matrix (FMC Corp., Rockland, Me.) are preferred. The gel concentration of choice will vary with the fragment length, but will typically be a concentration of between 4–6%. A gel thickness of 0.5 mm is recommended. Useful gel controls include fluorescent molecular weight markers, unreacted primer, full length PCR product, and a fluorescent sequencing reaction using control DNA.

For samples labeled with radioactive isotopes (preferably, $^{32}p$), a variety of denaturing gels can also be used for analysis. Again, a 19:1 acrylamide:bis-acrylamide gel mixture and Long Ranger gel matrix (FMC Corp., Rockland, Me.) are preferred, and the gel concentration, although varying with fragment length, will typically be between 4–8%.

Before radioactive sample loading, a portion of the samples are preferably counted by scintillation methods, and each lane in the gel preferably loaded with a minimum of 80–400 dps (and preferably 250 dps) for good overnight development of the autoradiogram, using Kodak X-omat AR or similar quality film. Use of an intensifier screen is also recommended.

Data Interpretation for Electrophoretic Analysis of Radiolabeled Cleavage Products If a mutation exists in a test sequence, heteroduplexes formed between the control and test sequences will contain a mismatch. The mismatch is recognized by T4 endonuclease VII, and a double-stranded cleavage occurring within 6 base pairs 3' to the mutation site is catalyzed. Two fragments therefore result from a duplex substrate containing a single base mismatch. Accordingly, if only one end of the duplex molecule is labeled, only one cleavage product is detected. If more than one cleavage site exists in a duplex (e.g., two mismatches), fragments from both cleavage sites can be detected if a limited digest is performed.

To locate the site of a mutation in a test sample, cleavage fragments of the DNA substrate are analyzed for size. As noted above, the site of cleavage will generally occur within 6 base pairs 3' to the mismatch site, although sequence context has some effect on site preference (Kleff and Kemper, EMBO J. 7:1527 (1988); Youil et al., Proc. Natl. Acad. Sci. USA 92:87 (1995)). Fragment size may be determined by gel electrophoresis of the cleavage fragments along with appropriate size markers, with a sequencing reaction of the control DNA being a preferred marker.

In addition, because T4 endonuclease VII is an enzyme that recognizes DNA structural features (including branching and single base pair mismatches and bends), some native DNA sequences assume structures that are cleaved by this enzyme. Accordingly, a homoduplex sequence is a useful control in these cleavage experiments.

Data Interpretation for Analysis of Fluorescently Labeled Cleavage Products

Figure 1:
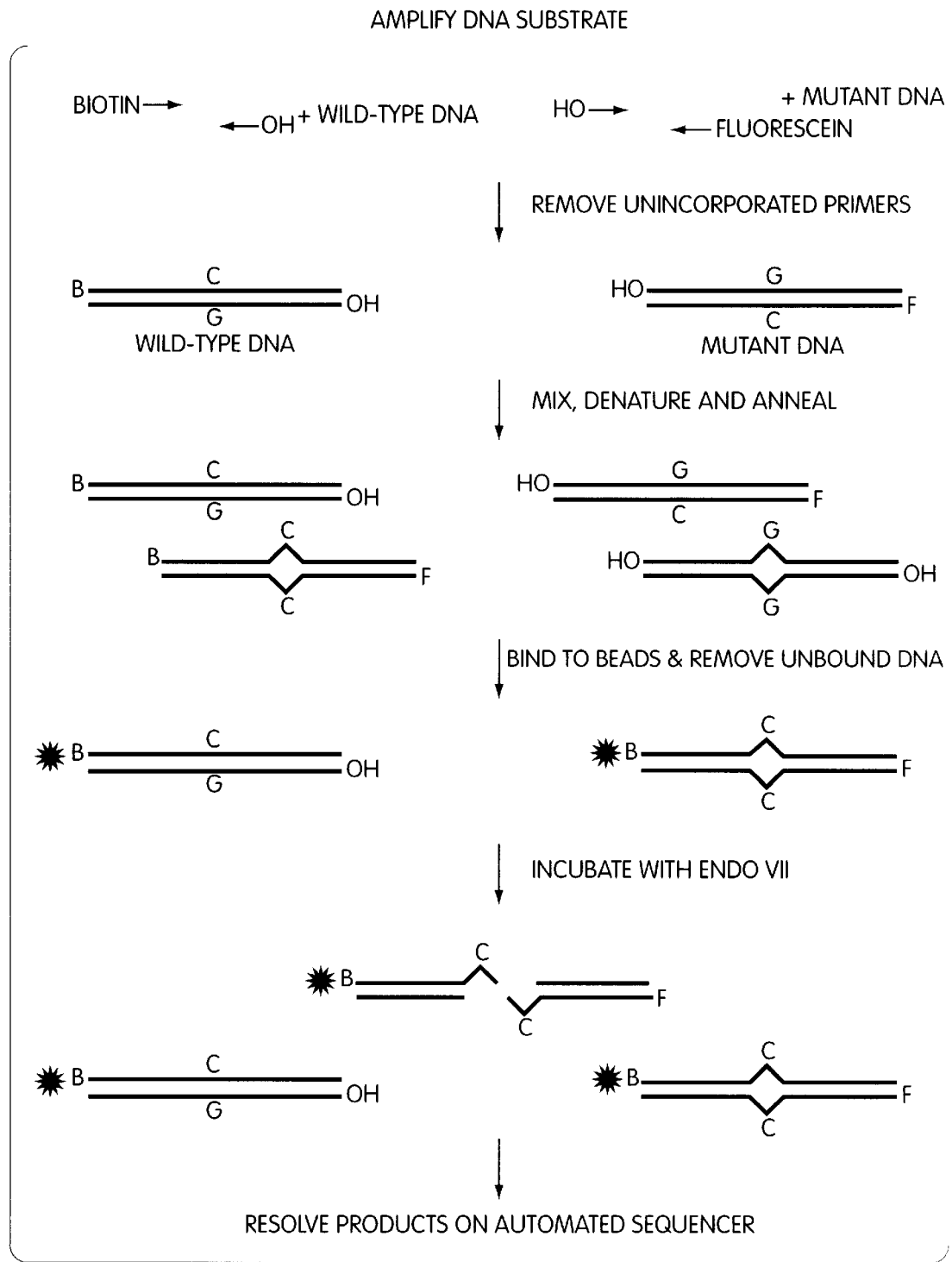
FIG. 1 is a flow chart representation of a fluorescence-based assay according to the invention. In this assay, a single fluorescent marker is employed, and only one PCR-amplified nucleic acid is biotinylated.
Figure 2:
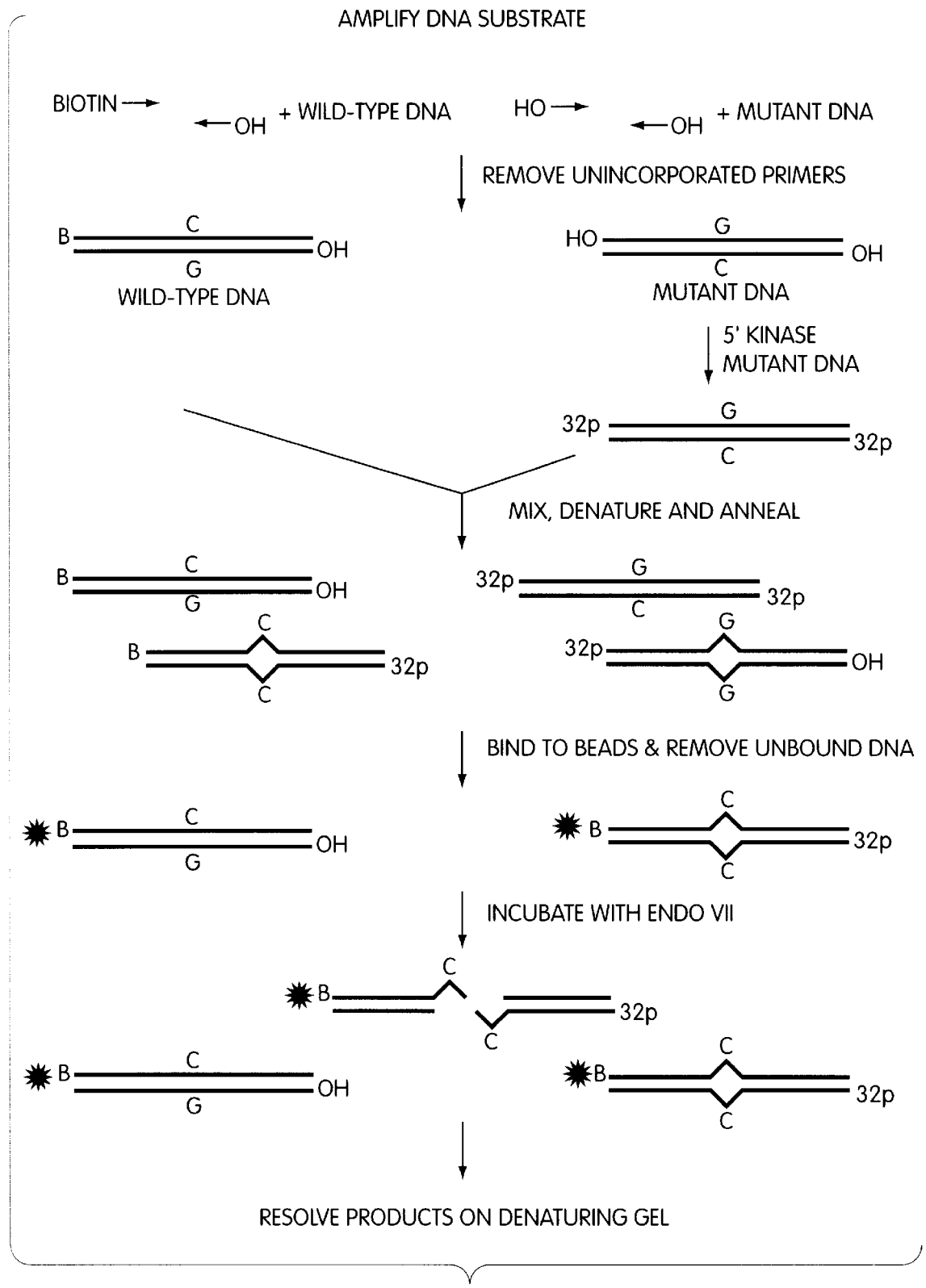
FIG. 2 is a flow chart representation of a radioactivity-based assay according to the invention. In this assay, a single PCR-amplified nucleic acid is biotinylated.
Figure 3:
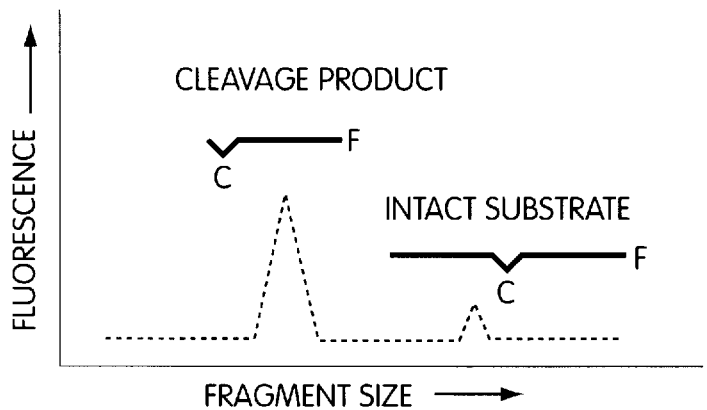
FIG. 3 is a schematic representation of the detection step involved in a fluorescent-based assay of FIG. 1. In particular, this figure illustrates the visualization of fluoresceinated products using an automated sequencer.
Figure 4:
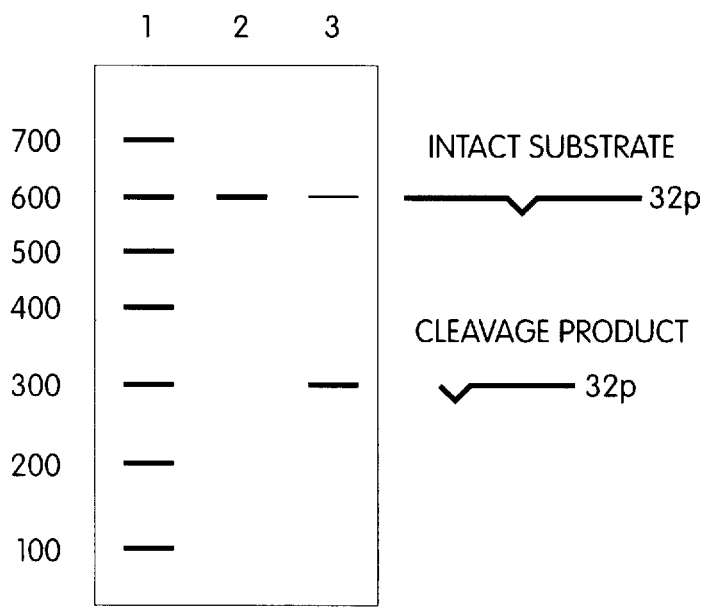
FIG. 4 is a schematic representation of the detection step involved in a radioactivity-based assay of FIG. 2. In particular, this figure illustrates the visualization of radioactive products using denaturing gel electrophoresis followed by autoradiography.
Figure 5:
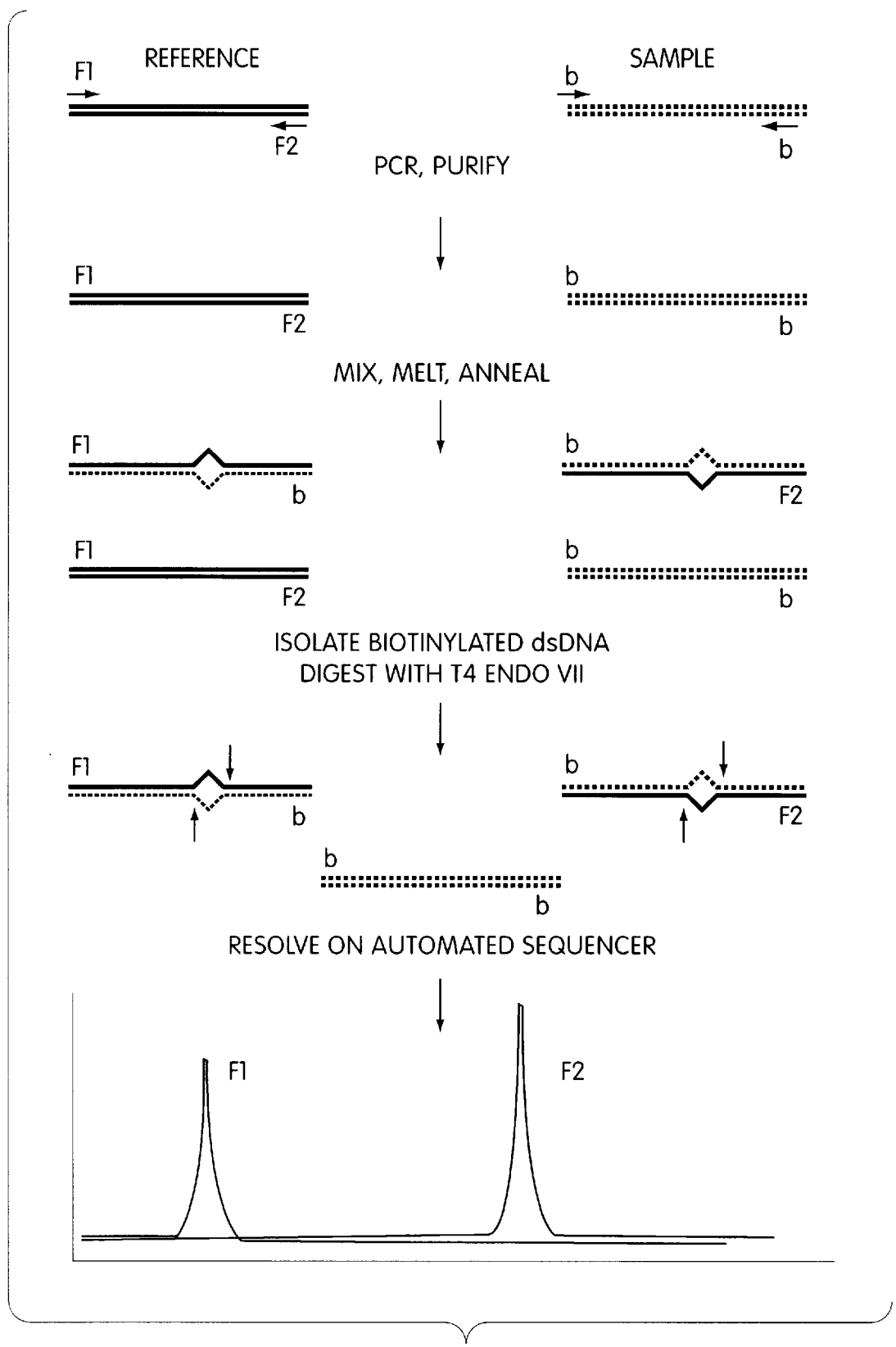
FIG. 5 is a flow chart representation of a fluorescence-based assay according to the invention. In this assay, two fluorescent markers are employed, and both strands of the PCR-amplified nucleic acid are biotinylated.
Figure 6:
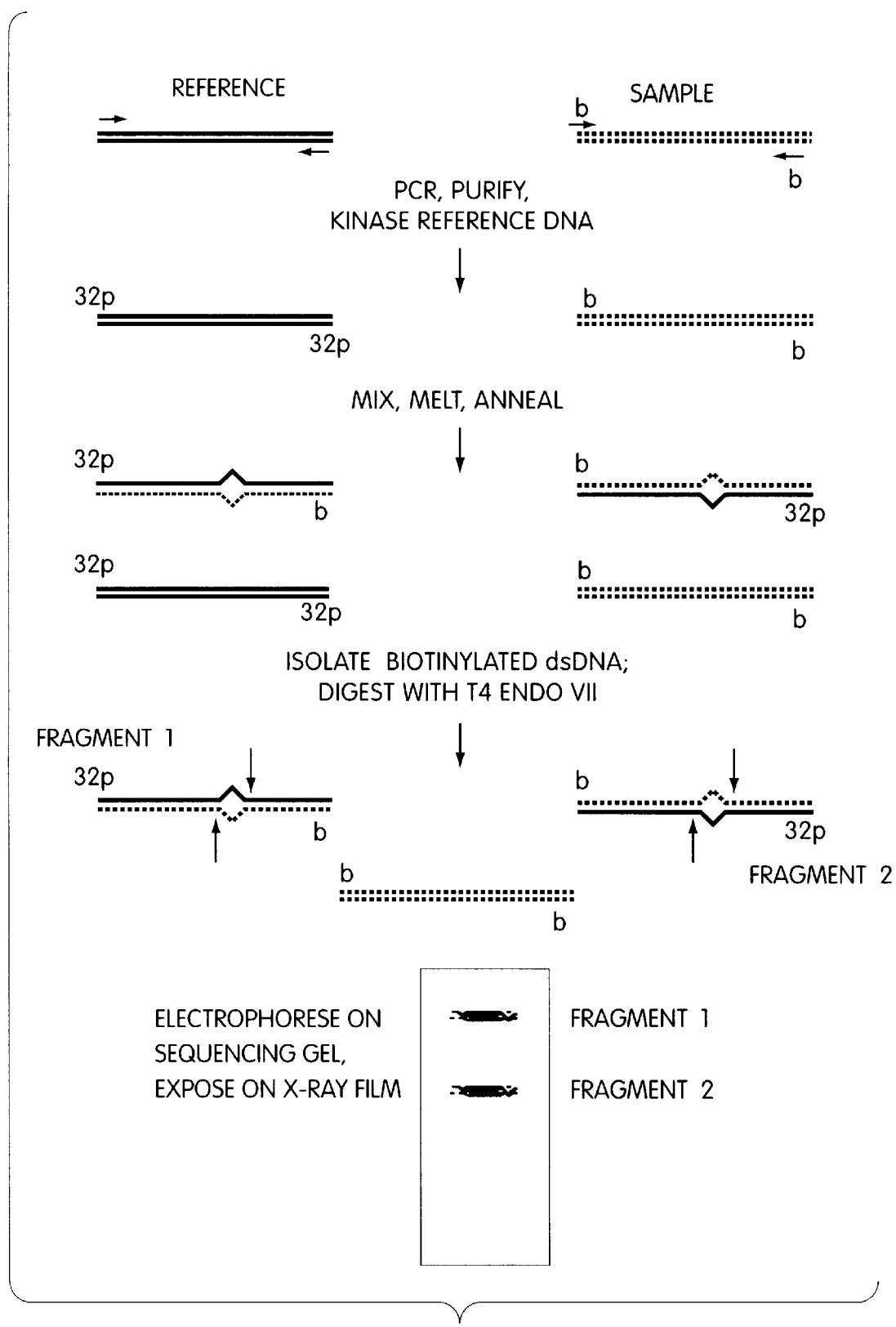
FIG. 6 is a flow chart representation of a radioactivity-based assay according to the invention. In this assay, both strands of the PCR-amplified nucleic acid are biotinylated.

FIG. 3 illustrates an idealized tracing from an automated sequencer. The cleavage product is a single band which passes through the laser window before the full length product. The exact size of the fragment can be determined from the time in minutes that it takes a fragment to pass the window. This "time to peak" parameter allows the automated sequencer to determine the nucleotide size of the fragment based on a control sequencing reaction. The intensity of the band can be used to calculate the extent of the cleavage reaction for an individual peak. The fluorograph feature of the automated sequencer allows the integration of peak area. For accurate determinations, it is preferable to base calculations on peaks which remain within the range of the fluorescence measurement. Fluorescence intensity titrations with primers (as recommended above) also increases the accuracy of these measurements.

Trouble Shooting

To optimize the utility of the claimed methods, there is now provided a series of steps at which performance of the assay may be compromised and suggestions for correcting these steps.

PCR Product is Contaminated with Non-Target PCR Products

Amplification of non-target sequences may be eliminated by optimizing the amplification conditions (see, for example, Perkin Elmer Technical Services, Foster City, Calif.). The optimal magnesium concentration, annealing temperature, and primer concentrations often need to be determined empirically for each primer/template combination. If optimizing the amplification conditions do not provide pure product, different primers may be designed.

Quantity of PCR Product is Low

Primer concentrations, magnesium concentration, dNTP concentration, or amount of enzyme may be inadequate. Generally primer concentrations should be between 0.2 to 0.5 $\mu$M. Magnesium concentration for AmpliTaq™ is normally between 1 mM and 4 mM; other enzymes may have different magnesium requirements. dNTP requirements will vary according to the amount of template, primers, and enzyme, with the optimal concentration normally ranging between 100 and 200 mM. The enzyme requirements for a particular primer/template set may have to be determined empirically; the AmpliTaq™ enzyme generally functions well at 2.5 units per 100 $\mu$l reaction mix.

PCR Product Contains Primer Dimer Contamination

To eliminate this problem, annealing temperature may be raised to decrease primer interaction, or, alternatively, primers may be redesigned. If primer dimer is the only non-target product present, it may be possible to remove the contamination by gel purification, or other post-amplification purification techniques.

Specific Activity of the Labeled PCR Product is Low

As a first step toward eliminating this problem, DNA quantification data is studied to ensure that the amount of DNA being labeled is correct. Primers are next examined. Only nonphosphorylated primers will label efficiently, and usage of the bacteriophage T4 polynucleotide kinase exchange reaction to label phosphorylated primers will result in much lower specific activities.

The procedure used to purify the PCR product should also be reviewed for possible sources of contamination with EDTA, phosphate, or ammonium ions, or other enzyme inhibiting or degrading substances. Moreover, contamination of PCR product with amplification primers will greatly reduce the specific activity of the desired product. Accordingly, the purification technique utilized should remove all unincorporated primers.

In addition, DNA purified from agarose gels may not end-label well, and this step of the procedure may be revised. Alternatively, because the procedure described herein does not use standard conditions for end-labeling (i.e., low levels of [$\gamma$-$^{32}$P]ATP are utilized) and because bacteriophage T4 polynucleotide kinase requires a concentration of 1 $\mu$M ATP to function optimally ($\approx$100 $\mu$Ci at 3000 Ci/mmol in a 20 $\mu$l reaction), the specific activity of the PCR product may be significantly increased by using optimum [$\gamma$-$^{32}$P]ATP conditions. Finally, the activity of the T4 polynucleotide kinase should be examined to ensure that the enzyme is fully active.

DNA Does Not Bind Well to the Dynabeads

To remedy this problem, the primers should first be examined to ensure that at least one primer being used is biotinylated. In addition, the binding and washing buffer should be checked, and the beads examined for proper washing prior to use. Poor binding may also result from small amounts of contamination from unincorporated biotinylated primers left over from the PCR reaction, as these primers will bind to the beads very efficiently and lower the binding capacity of the beads for PCR product. Finally, inadequate agitation during the binding period may result in incomplete binding.

Endo VII Digestion

If no Endo VII digestion of heteroduplex or homoduplex DNA is detected in experimental samples, positive control heteroduplex DNA should be digested to determine if the reaction proceeds normally. Also, the samples should be checked to be sure that the substrate for the enzyme has a mismatch (for example, by sequencing the putative positive control). If no digestion is observed in the control heteroduplex sample, the storage and handling conditions of the enzyme should be examined. Endo VII is temperature-sensitive, and all handling instructions should be observed. In addition, the enzyme dilution procedure should be reviewed to ensure that the enzyme was diluted with the correct buffer and to the specified concentration. The use of the proper reaction buffer should also be confirmed.

Experimental Sample Has Cleavage Product(s) in Both the Control and Heteroduplex Sample T4 endonuclease VII does show some sequence-specific cleavage. Accordingly, the heteroduplex sample should be checked for the presence of an additional band that is not present in the homoduplex sample. If this extra band is clearly visible and distinct, the assay is working, and a slight reduction in the amount of enzyme may reduce the amount of unwanted cleavage. Correct function of the enzyme cleavage system may be verified by performing a reaction using control DNA containing a known mismatch, and analysis of a sample of undigested experimental DNA on a gel may be performed to ensure that the substrate is intact and produces a single, tight band.

Experimental Results

To qualitatively assess the above technique, five different point mutations (-2A, -27G, -34G, -42A, -43A) in a plasmid library of single base pair mutations were chosen spanning a 132 bp segment of the mouse $\beta$-globin promoter region, a region that was previously shown to have a high level of background cleavage. A 546 bp fragment of this region was amplified from a plasmid library by PCR using the 5' primer (5'-gcacgcgctggacgcgcat) (SEQ ID NO: 1) and the 3' primer (5'-aggtgcccttgaggctgtcc) (SEQ ID NO: 2) for the wild type clone, and the same primers, but each with biotinylated 5' ends for the five different mutant clones (as well as for the wild type homoduplex control). The PCR conditions in all cases were 95° C. for 2 minutes, 65° C. for 3 minutes, and 72° C. for 2 minutes over 30 cycles. The PCR products were then purified, and the unbiotinylated wild-type PCR products radiolabeled as described previously (Youil et al., Proc. Natl. Acad. Sci. USA 92:87 (1995)).

Heteroduplexes were then formed by annealing radiolabeled wild type DNA to excess mutant DNA in an approximately 1:2 molar ratio under conditions also described previously (Youil et al., supra) A sample containing 7.5 $\mu$g of Dynabeads M-280 Streptavidin (pre-washed and resuspended in PBS/0.1% albumin at a concentration of 0.5 mg/ml) was added to 100–250 ng of heteroduplex DNA. This was incubated at room temperature for 30 minutes on a rotator. The Dynabeads (now bound to biotinylated DNA) were then pelleted using a magnet, washed 2–3 times with TE buffer and resuspended in TE. This substrate was then incubated in the presence of 100 units of T4 endonuclease VII as previously described (Youil et al., supra) but in a 37° C. shaker for 45 minutes. The reaction was stopped by adding a half-volume of loading dye (Youil et al., supra) and heating to 72° C. (to allow dissociation of the biotinylated DNA from the Dynabeads). The beads were pelleted using a magnet, and the supernatant loaded onto an 8% denaturing (19:1, acrylamide:bis-acrylamide, 8.3M urea) polyacrylamide gel. These gels were run in TBE buffer at 45 W for 90 minutes, then dried and visualized by autoradiography.

The five β-globin promoter mutations, when investigated using conventional enzyme mismatch cleavage, ranged from producing a strong (-27G) to a medium (-34G, -42A) to a weak signal (-2A, -43A). The signal to noise ratios for these mutations were in each case improved using this new method, although the classifications of strong, medium, and weak still generally applied (see FIGS. 7A–7C). Because T4 endonuclease VII cleaves many secondary structures in DNA, the background cleavage observed is most likely due to DNA secondary structure. Discarding the homoduplex DNA removes most of the source of background cleavage, but secondary structures on the heteroduplexes are also substrates for background cleavage. Accordingly, although a low but detectable noise level is still detectable, this modification ensures that a poor heteroduplex yield after the melting/re-annealing step will not result in the signal being obscured by a high noise level. As such, this modification selects for heteroduplexes and thus removes background resulting from labeled homoduplexes. As shown in FIGS. 7A–7C, depending on the resolving power of the gel and the position of the mutation, two cleavage fragments are visible for each mutation, as both heteroduplexes are radiolabeled and biotinylated. As discussed above, it is possible to target just one of the heteroduplexes by amplifying the mutant using only one biotinylated primer (the other being unbiotinylated). In this way, only one of the two heteroduplexes will bind to the Dynabeads. This alteration increases the signal to noise ratio even further, but only one of the two fragments will be detected. Alternatively, by employing different fluorescent labels on the primers used to PCR amplify the wild type DNA, the two resultant heteroduplexes are easily distinguishable from each other and can be separated and visualized on an automated sequencing apparatus. In addition, because the reaction is performed on a solid phase, this process lends itself well to automation.

Other Embodiments

Other embodiments are within the following claims. For example, any magnetic bead-type solid support may be utilized in the invention; such beads include, without limitation, Dynabeads (Dyna, Oslo, Norway), BioMag Streptavidin (Advanced Magnetics, Cambridge, Mass.), MPG® Streptavidin (CPG, Inc., Lincoln Park, N.J.), Streptavidin Magnesphere™ (Promega, Madison, Wis.), Streptavidin Magnetic Particles (Boehringer Mannheim Corp., Indianapolis, Ind.), AffiniTip™ (Genosys Biotechnologies, Inc., Woodlands, Tex.), any of the Maga line of magnetizable particles (Cortex Biochem, San Leandro, Calif.), BioMag Superparamagnetic Particles (PerSeptive Biosystems, Framingham, Mass.), and magnetic beads from Sigma Chemical Co. (St. Louis, Mo.). Materials for use with these beads may be obtained, for example, from Bangs Laboratories (custom and off-the-shelf surface chemistries; Carmel, Ind.), GMW (high-field electromagnets; Redwood City, Calif.), Immunicon (ferrofluid magnetic separations; Huntington Valley, Pa.), Miltenyi Biotec (MACS Magnetic Separation System; Cologne, Germany; Auburn, Calif.), and Techne (Beadprep 96 magnetic separator; Redwood City, Calif.; Cambridge, U.K.). If non-magnetic streptavidin-bound solid supports are utilized, they may be obtained, without limitation, from Seradyn (Indianapolis, Ind.; Power-Bind™ Streptavidin), Boehringer Mannheim Corp. (Indianapolis, Ind.), Pierce Chemical Co. (Rockford, Ill.; streptavidin-coated microtiter plates), or Xenopone Corp. (Saddle Brook, N.J.; streptavidin-coated microtiter plates).

The binding of a PCR product to the magnetic bead may be varied and may be accomplished through any desired covalent or non-covalent specific binding pair. Such binding pairs are well known in the art and include any pair involving nucleic acid or protein components that are not denatured or separated under the conditions employed in the assay; such pairs include antigen/antibody pairs, DNA binding protein/DNA binding site pairs (for example, the GCN4 protein and its DNA binding site), enzyme/substrate pairs, lectin/carbohydrate pairs, and base paired or ligated nucleic acids. A preferred specific binding pair according to the invention is avidin/biotin.

Moreover, if desired, many of the steps described above may be modified or excluded from the procedure. For example, the particular radioactive or fluorescent labels described above may be replaced by any one or more detectable labels, for example, any radioactive, fluorescent, chemiluminescent, or chromogenic labels which may be directly or indirectly visualized; also included as useful labels are haptens, such as digoxigenin, that are recognized by antibodies that are themselves detectably labelled. In addition, heteroduplexes may be formed prior to radioactive labeling, and the labeling step carried out either just prior to resolvase cleavage or after resolvase cleavage (taking advantage of the freshly exposed ends for labeling).

Magnetic bead binding and cleavage reaction conditions may also be varied as well known by those skilled in the art. For example, the binding capacity of the Dynabeads M-280 streptavidin described herein is directly related to the length of the DNA species being captured, with DNA binding capacity being reduced as DNA length increases (as a consequence of steric hindrance) (see, for example, the Dynabeads M-280 streptavidin product insert, Dynal, Inc.). In addition, Endo VII activity is affected by DNA sequence, length, and quantity. Accordingly, for any given reaction, binding capacity is first determined for each DNA species being captured, and bead volume appropriately adjusted. In addition, the units of Endo VII required to generate between 25–100% cleavage are determined for a particular substrate. Once these bead volumes and enzyme amounts are determined for a specific DNA, unknown samples may be screened using these predetermined conditions.

If different fluorophores are utilized in the techniques of the invention, multiple mutations may be detected simultaneously, for example, by PCR amplifying different regions of a DNA sample (for example, different exons of interest) using PCR primers that are each labeled with a unique fluorophore that is detectable in the presence of the other fluorescent tags (for example, using an ABI automated sequencing system).

The invention may be carried out using any desired resolvase. Although T4 endonuclease VII is preferred, other resolvases useful in the invention include, without limitation, bacteriophage T7 Endonuclease I and Saccharomyces cerevisiae Endo X1, Endo X2, or Endo X3 (Jensch et al., EMBO J. 8:4325, 1989), T7 endonuclease I, *E. coli* MutY (Wu et al., Proc. Natl. Acad. Sci. USA 89:8779–8783, 1992), mammalian thymine glycosylase (Wiebauer et al., Proc. Natl. Acad. Sci. USA 87:5842–5845, 1990), topoisomerase I from human thymus (Yeh et al., J. Biol. Chem. 266:6480–6484, 1991; Yeh et al., J. Biol. Chem. 269:15498–15504, 1994), and deoxyinosine 3' endonuclease (Yao and Kow, J. Biol. Chem. 269:31390–31396, 1994). Mismatch detection assays may be carried out using one or a combination of different resolvases. If necessary, the methods and kits of the invention allow for convenient sequential resolvase reactions using different buffer conditions.

The test nucleic acid and/or the reference nucleic acid may be derived from any eukaryotic cell, eubacterial cell, bacteriophage, DNA virus, or RNA virus. Preferred RNA viruses include, without limitation, human T-cell leukemia virus and human immunodeficiency virus (for example, HTLV-I, HTLV-II, HIV-1, and HIV-2). Preferred DNA viruses include, without limitation, any one of the family Adenoviridae, Papovaviridae, or Herpetoviridae. Preferred eubacterial cells include, without limitation, any member of the order Spirochaetales, Kinetoplastida, or Actinomycetales, of the family Treponemataceae, Trypoanosomatidae, or Mycobacteriaceae, and of the species *Mycobacterium tuberculosis, Treponema pallidum, Treponema pertenue, Borrelia burgdorferi,* or *Trypanosoma cruzi.*

The reference nucleic acids may also include an oncogene or a tumor suppressor gene of a eukaryotic (for example, mammalian) cell; preferable mammalian oncogenes include, without limitation, abl, akt, crk, erb-A, erb-B, ets, fes/fps, fgr, fms, fos, jun, kit, mil/raf, mos, myb, myc, H-ras, K-ras, rel, ros, sea, sis, ski, src, and yes; preferable tumor suppressor genes include p53, retinoblastoma (preferably RB1), adenomatous polyposis coli, NF-1, NF-2, MLH-1, MTS-1, MSH-2, BRCA-1, BRCA-2, ATM, and human nonpolyposis genes.

Alternatively, the reference nucleic acid may be isolated from any one of the β-globin, $\alpha_1$-antitrypsin, 21-hydroxylase, pyruvate dehydrogenase E1α-subunit, dihydropteridine reductase, rhodopsin, β-amyloid, nerve growth factor, superoxide dismutase, Huntington's disease, cystic fibrosis, adenosine deaminase, β-thalassemia, ornithine transcarbamylase, collagen, bcl-2, β-hexosaminidase, topoisomerase II, hypoxanthine phosphoribosyltransferase, phenylalanine 4-monooxygenase, Factor VIII, Factor IX, nucleoside phosphorylase, glucose-6-phosphate dehydrogenase, phosphoribosyltransferase, Duchenne muscular dystrophy, von Hippel Lindeau, or the mouse mottled Menkes genes. Reference nucleic acids may also be derived from any cell cycle control gene, preferably p21, p27, or p16.

The reference nucleic acid may be any nucleic acid molecule including, without limitation, a restriction enzyme fragment, a sequence produced by amplification via PCR, NASBA, SDA, or any other preparative amplification method, or a sequence propagated in any eukaryotic cell, bacteriophage, eubacterial cell, insect virus (e.g., using a baculovirus derived vector), or animal virus (e.g., using an SV-40 or adenovirus derived vector).

Any test DNA template suspected of harboring at least one DNA mutation and for which at least a partial DNA sequence is known can be used as a source of PCR-amplified test DNA. A DNA template for this purpose must include a region suspected of harboring at least one DNA mutation and must also include sufficient DNA flanking the suspected mismatch to serve as a template for DNA oligonucleotide primer hybridization and PCR amplification. As outlined above, PCR amplification is performed by first hybridizing two oligonucleotide primers to the template harboring the mutation, then completing multiple rounds of PCR amplification. The design of the two oligonucleotide primers is guided by the DNA sequence flanking the suspected mutation site and two important parameters: DNA oligonucleotide primer size and the size of the intervening region between the 3' ends of the DNA oligonucleotide primers hybridized to the template. Preferably, an oligonucleotide primer will be at least 12 nucleotides in length, more preferably, between 15 and 50 nucleotides in length inclusive, and most preferably, between 15 and 25 nucleotides in length inclusive. The size of the intervening region between the 3' ends of the two oligonucleotides hybridized to the template will be governed by the well known size limitations of templates amplified by PCR and the resolving power of the particular gel used to detect resolvase cleavage sites. In general, the intervening region between the 3' ends of the two oligonucleotides hybridized to a template will be at least 50 base pairs in length inclusive. Recent advances in PCR technology have allowed amplification of up to 40 kb of DNA. Preferably, the intervening region will be between 100 and 40,000 base pairs in length inclusive, and more preferably between 150 and 5000 base pairs in length inclusive. Those skilled in the art will appreciate that where the flanking DNA sequence is only partially known, a degenerate DNA oligonucleotide primer may be used to prepare test DNA by PCR amplification.

In another example, template DNA suspected of harboring at least one DNA mutation can be subcloned into a suitable cloning vector and amplified using known DNA oligonucleotide primers which hybridize to the cloning vector and are adjacent to the insertion site of the DNA template. In this instance, no template DNA sequence information is required because the DNA oligonucleotide primers used for PCR amplification hybridize to a vector of known DNA sequence and not the inserted template DNA. For example, the Bluescript™ vector can be used to sub-clone a DNA template into an acceptor site according to the manufacturer's instructions (Stratagene Cloning Systems, La Jolla, Calif., Product Catalogue, (1992)). The T7 and T3 DNA primers of the Bluescript vector can be used to PCR amplify the inserted DNA template (or concomitantly to sequence the inserted DNA template). Other commercially available sub-cloning vectors may also be used. These include, without limitation, phage lambda based insertion vectors and other prokaryotic and eukaryotic vectors (e.g., bacteriophage, insect virus, or animal virus based vectors described by Stratagene, supra and Sambrook et al., supra).

In an alternative method, a vector which includes a DNA insert bearing at least one DNA mutation may be first amplified by propagation in bacteria, phage, insect, or animal cells prior to PCR amplification (see Sambrook et al., supra). If sufficient DNA is available (i.e., at least 1 nanogram), the PCR amplification step can be eliminated.

In yet another example, RNA suspected of bearing at least one mutation may be purified from cells or tissues by techniques well-known in the art. For example, RNA may be optionally purified by olido-dT chromatography to prepare mRNA (see, for example, Sambrook et al., supra and Ausubel et al., supra). In cases where ribosomal RNA is the subject of analysis or a particular mRNA is in abundance, oligo-dT chromatography will not be necessary. Purified RNA or mRNA will be heat denatured in order to ensure complete single-strandedness and hybridized with control DNA (i.e., a reference cDNA) in order to form RNA:DNA heteroduplexes. A method for forming RNA:DNA duplexes are well known in the art and have been described in detail (see Sambrook et al., supra, pp. 7.62–7.65). After formation of an RNA:DNA heteroduplex, the method described above may be used to detect mismatches produced by mispairing between the cDNA and the RNA.

Individuals skilled in the art will readily recognize that the compositions of the present invention can be assembled into a kit for the detection of mismatches. Typically, such kits will include at least one resolvase capable of detecting a mismatch and a magnetic bead to which is bound one member of the desired specific binding pair. Preferably, the kit will include bacteriophage T4 endonuclease VII in a suitable buffer and will optionally include either appropriately labelled reference DNA or appropriately labelled reference and/or test DNA primers (i.e., reference DNA or PCR primers labelled with the other member of the specific binding pair and/or a detectable label). The kit may also include pre-formed heteroduplexes with which to standardize reaction conditions and/or appropriate buffers (for example, enzyme dilution buffers or enzyme reaction buffers).

Mismatch detection using a solid support and the above methods may be used in combination with any resolvase cleavage technique, for example, the resolvase cleavage techniques described in Cotton et al., U.S. Ser. No. 08/232,530, hereby incorporated by reference.

a) providing a magnetic bead to which is bound, through a specific binding pair, a duplex comprising said first and said second nucleic acids, said duplex being further bound to a detectably labelled reagent;

b) separating said magnetic bead and bound products from the remainder of a sample containing said magnetic beads;

c) contacting said magnetic bead-bound nucleic acid with a resolvase capable of recognizing at least one single base pair mismatch in a heteroduplex, under conditions which permit said resolvase to cleave said heteroduplex; and d) analyzing said product of step (c), the presence of a cleavage product being an indication of a mismatch between said first and said second nucleic acids.

2. The method of claim 1, wherein said magnetic bead is a streptavidin-coated magnetic bead.

3. The method of claim 1, wherein said product of step (f) is analyzed by gel electrophoresis or other detectable signal intensity method.

4. The method of claim 1, wherein said product of step (f) is analyzed by radioactive scintillation counting or fluorescence detection.

5. The method of claim 1, wherein said resolvase is bacteriophage T4 endonuclease VII.

6. The method of claim 1, wherein said first or said second nucleic acid is the product of PCR amplification.

7. The method of claim 6, wherein said first nucleic acid is PCR amplified using at least one primer labelled with said first member of said specific binding pair.

What is claimed is:

1. A method for detecting one or more mismatches between a first and a second nucleic acid, said first and said second nucleic acids being capable of preferentially hybridizing, said method comprising:

8. The method of claim 6, wherein said first nucleic acid is amplified using one primer labelled with said first member of said specific binding pair and a second primer which is unlabelled.

9. The method of claim 7, wherein said specific binding pair is avidin and biotin.

10. The method of claim 1, wherein said first or said second nucleic acids are rendered single-stranded by denaturation.

11. The method of claim 6, wherein said second nucleic acid is detectably labelled during PCR amplification.

12. The method of claim 11, wherein said detectable label is a radioactive, fluorescent, or other detectable label.

13. The method of claim 1, wherein said mismatch results from a mutation or polymorphism.

14. The method of claim 1, wherein one of said first or said second nucleic acids comprises a reference nucleic acid and the other comprises a test nucleic acid.

15. A method for detecting one or more mismatches between a first and a second nucleic acid, said first and said second nucleic acids being capable of preferentially hybridizing, said method comprising:
   a) providing a duplex comprising said first and said second nucleic acids, said first nucleic acid being bound to the first member of a specific binding pair;
   b) contacting said duplex with a magnetic bead to which is bound a second member of said specific binding pair under conditions allowing complex formation between said first and said second members of said specific binding pair;
   c) separating said magnetic bead and bound products from the remainder of said product of step (b);
   d) contacting said magnetic bead-bound nucleic acid with a resolvase capable of recognizing at least one single base pair mismatch in a heteroduplex, under conditions which permit said resolvase to cleave said heteroduplex; and
   e) analyzing the supernatant of step (d), the presence of a cleavage product being an indication of a mismatch between said first and said second nucleic acids.

16. The method of claim 15, wherein said analyzing in step (g) comprises electrophoresis.

17. The method of claim 16, wherein said electrophoresis is followed by silver staining of the electrophoretic gel.

18. A method for detecting one or more mismatches between a first and a second nucleic acid, said first and said second nucleic acids being capable of preferentially hybridizing, said method comprising:
   a) providing a duplex comprising said first and said second nucleic acids, said first nucleic acid being bound to the first member of a specific binding pair;
   b) contacting said duplex with a magnetic bead to which is bound a second member of said specific binding pair under conditions allowing complex formation between said first and said second members of said specific binding pair;
   c) separating said magnetic bead and bound products from the remainder of said product of step (b);
   d) contacting said magnetic bead-bound nucleic acid with a resolvase capable of recognizing at least one single base pair mismatch in a heteroduplex, under conditions which permit said resolvase to cleave said heteroduplex;
   e) labeling the product of step (d) not bound to said magnetic bead with a detectable label; and
   f) analyzing said labeled product, the presence of a cleavage product being an indication of a mismatch between said first and said second nucleic acids.

19. A method for detecting one or more mismatches between a first and a second nucleic acid, said first and said second nucleic acids being capable of preferentially hybridizing, said method comprising:
   a) providing a magnetic bead to which is bound, through a specific binding pair, a duplex comprising said first and said second nucleic acids, said duplex being further bound to a detectably labelled reagent;
   b) separating said magnetic bead and bound products from the remainder of a sample containing said magnetic beads;
   c) contacting said magnetic bead-bound nucleic acid with a resolvase capable of recognizing at least one single base pair mismatch in a heteroduplex, under conditions which permit said resolvase to cleave said heteroduplex; and
   d) analyzing the product found in the sample supernatant of step (c), the presence of a cleavage product being an indication of a mismatch between said first and said second nucleic acids.

20. A kit for detecting a mismatch in a test nucleic acid, said kit comprising:
   a) a magnetic bead to which is bound one member of a specific binding pair; and
   b) a resolvase which is capable of recognizing and cleaving at least one single base pair mismatch in a heteroduplex.

21. The kit of claim 20, further comprising a reference nucleic acid which preferentially hybridizes to said test nucleic acid, said reference nucleic acid being capable of binding to the second member of said specific binding pair.

22. The kit of claim 20, further comprising a pair of PCR primers, at least one primer of said pair being capable of binding to said second member of said specific binding pair.

23. The kit of claim 20, further comprising a pair of PCR primers, at least one primer of said pair being bound to a detectable label.

24. The kit of claim 20, wherein said specific binding pair is avidin and biotin.

25. The kit of claim 20, wherein said resolvase is bacteriophage T4 endonuclease VII.

26. The kit of claim 20, wherein said magnetic bead is a streptavidin-coated magnetic bead.

27. The method of claims 1, 15, 18, or 19, wherein said first or said second nucleic acid is derived from a eukaryotic cell, a eubacterial cell, a bacterial cell, or a virus.

28. The method of claim 27, wherein said eukaryotic cell is a human cell.

29. The method of claims 1, 15, 18, or 19, or wherein each of said first and said second nucleic acids is at least 100 nucleotides in length.

* * * * *

UNITED STATES PATENT AND TRADEMARK OFFICE
CERTIFICATE OF CORRECTION

PATENT NO. : 5,851,770
DATED : December 22, 1998
INVENTOR(S) : Jeff Babon et al.

It is certified that error appears in the above-identified patent and that said Letters Patent is hereby corrected as shown below:

Column 6,
Line 15, replace "supra" with -- supra --;

Column 9,
Lines 30 and 31, replace "supra" with -- supra --;
Lines 33 and 34, replace "supra" with -- supra --;
Line 42, replace both occurrences of "supra" with -- supra --;

Column 11,
Lines 2 and 3, replace "Dynal® PC®-9600" with -- Dynal® MPC®-9600 --;
Line 66, replace "$10\mu M$" with -- 10mM --;

Column 12,
Line 47, replace "10MM" with -- 10mM --;

Column 16,
Line 63, replace "supra" with -- supra --;

Column 17,
Lines 5 and 7, replace "supra" with -- supra --;

Column 18, line 67 through Column 19, line 1,
Replace "Saccharomyces cerevisiae" with -- *Saccharomyces cerevisiae* --;

Column 20,
Lines 53, 58, 64 and 65, replace "supra" with -- supra --;

UNITED STATES PATENT AND TRADEMARK OFFICE
CERTIFICATE OF CORRECTION

PATENT NO.    : 5,851,770
DATED         : December 22, 1998
INVENTOR(S)   : Jeff Babon et al.

It is certified that error appears in the above-identified patent and that said Letters Patent is hereby corrected as shown below:

Column 21,
Line 6, replace "supra" with -- supra --.

Signed and Sealed this

Sixteenth Day of September, 2003

JAMES E. ROGAN
*Director of the United States Patent and Trademark Office*